(12) United States Patent
Kerpershoek et al.

(10) Patent No.: US 7,386,097 B2
(45) Date of Patent: Jun. 10, 2008

(54) ANALYTICAL INSTRUMENT WITH VARIABLE APERTURES FOR RADIATION BEAM

(75) Inventors: Gijsbertus J. Kerpershoek, Barendrecht (NL); Leendert J. Seijbel, Rotterdam (NL); Arjen B. Storm, Den Haag (NL); Arne Kasten, Karlsruhe (DE)

(73) Assignee: Broker AXS, Inc., Madison, WI (US)

( * ) Notice: Subject to any disclaimer, the term of this patent is extended or adjusted under 35 U.S.C. 154(b) by 142 days.

(21) Appl. No.: 11/257,765

(22) Filed: Oct. 25, 2005

(65) Prior Publication Data

US 2006/0108534 A1    May 25, 2006

(30) Foreign Application Priority Data

Oct. 28, 2004   (DE) .................. 10 2004 052 350

(51) Int. Cl.
*G21K 1/02* (2006.01)
(52) U.S. Cl. ........................ 378/149; 378/148
(58) Field of Classification Search ........ 378/145–146, 378/147, 148–149, 161, 84, 150
See application file for complete search history.

(56) References Cited

U.S. PATENT DOCUMENTS

| | | | | |
|---|---|---|---|---|
| 3,593,004 A * | 7/1971 | Ryan Jr. ................ 235/459 |
| 4,528,453 A | 7/1985 | Heller |
| 5,408,512 A * | 4/1995 | Kuwabara et al. ............ 378/45 |
| 6,337,897 B1 | 1/2002 | Kawahara et al. |
| 6,788,764 B2 * | 9/2004 | Saladin et al. .............. 378/152 |
| 2002/0039401 A1* | 4/2002 | Salb .......................... 378/98.9 |
| 2003/0081191 A1* | 5/2003 | Nishi et al. .................... 355/69 |

FOREIGN PATENT DOCUMENTS

| | | |
|---|---|---|
| DE | 102 57 206 A1 | 7/2004 |
| JP | 08285798 A | 1/1996 |
| JP | 10142171 A | 5/1998 |
| WO | WO01/44793 A2 | 6/2001 |

OTHER PUBLICATIONS

Bruker AXS, "Structural Biology Solutions, X8 Proteum X8 Prospector", Bruker Advanced X-Ray Solutions, 2005, pp. 1-25, Germany.

* cited by examiner

*Primary Examiner*—Hoon Song
(74) *Attorney, Agent, or Firm*—Law Offices of Paul E. Kudirka

(57) ABSTRACT

An X-ray analysis device makes use of a variable aperture for controlling the position and cross section of the X-ray beam. The variable aperture is configured to allow changes in the cross section and/or position of the beam by movement of one aperture component in one direction. In one embodiment, the aperture medium is a perforated disk that is rotated to expose different aperture holes to the beam. In another embodiment, the aperture medium is a perforated tape that is moved in a linear direction to expose different aperture holes to the beam. The tape may be wound about two axes to control its movement, or may be a continuous loop. A cassette may also be used to house the tape.

31 Claims, 7 Drawing Sheets

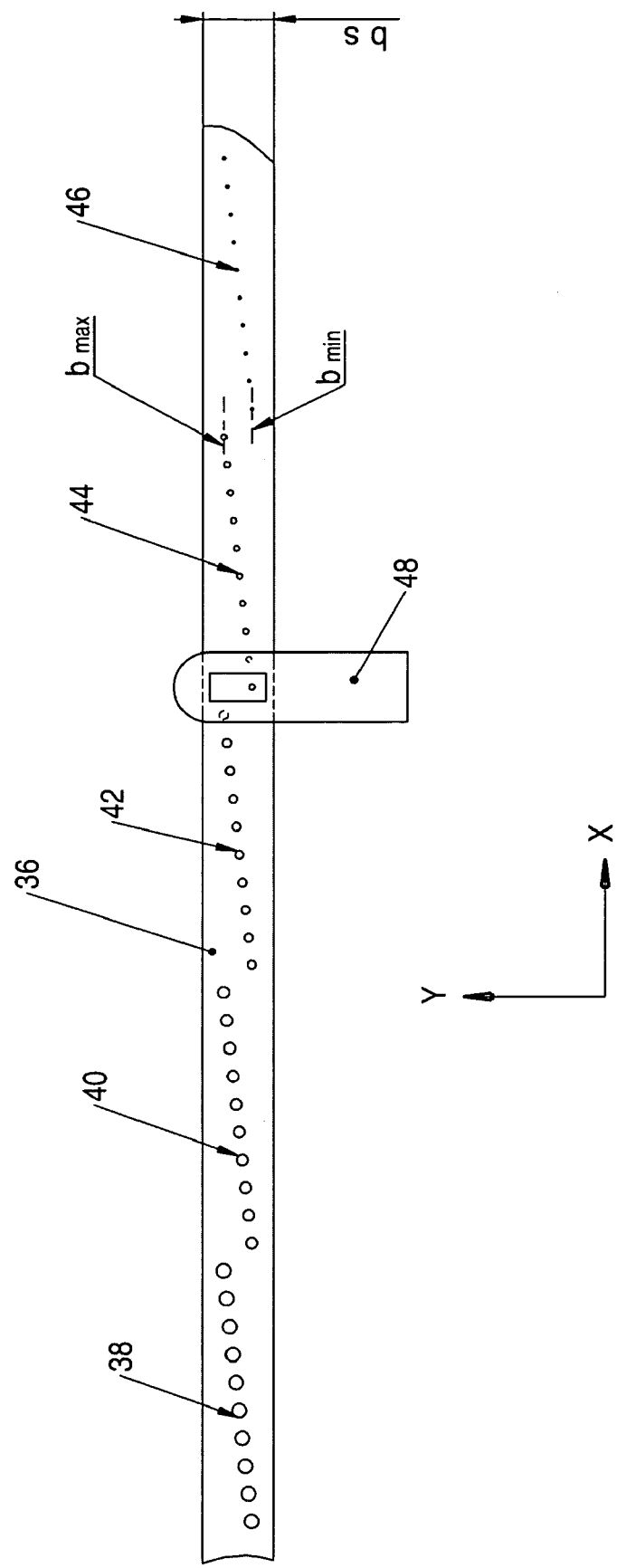

ANALYTICAL INSTRUMENT WITH VARIABLE APERTURES FOR RADIATION BEAM

FIELD OF THE INVENTION

This invention relates, generally to the use of variable apertures for high energy radiation in analysis equipment and, more specifically, variable apertures used for limiting the size and shape of an X-ray beam in a single crystal X-ray diffractometer.

BACKGROUND OF THE INVENTION

An X-ray optical device with a variable aperture is discussed in US Patent Application Publication No. US 2004/0170250 A1. In this device, the variable aperture consists of a fixed portion and a movable portion that moves relatively to the fixed portion to change the size of an opening formed between the portions. These portions together are capable of shaping an X-ray beam passed through the aperture to a rectangular cross-section. As the movable portion is moved, the cross-section and position of the X-ray beam output from the device are changed. Notably, it is not possible to change the beam position while maintaining a consistent cross-section, or to change the beam cross-section while maintaining the position, unless both portions of the aperture are exchanged for aperture portions of different configurations.

A known X-ray diffractometer (the "X8 Proteum" produced by Bruker AXS, Madison, Wis.) uses a beam aperture that is mounted in a holder so that it is positioned perpendicularly to an incident X-ray beam. The aperture limits the cross-section of the beam, and its position can be adjusted in two orthogonal directions prior to its being fixed in place. This allows a user to fine-tune the position of the transmitted beam as part of an initial setup. Different beam cross-sections may also be selected by choosing from apertures with different shapes. However, to accomplish any of these changes requires time-consuming adjustments of the aperture, either by repositioning in two independent directions or by the manual exchange of the aperture.

SUMMARY OF THE INVENTION

In accordance with the present invention, an analysis apparatus that uses a radiation beam that illuminates a sample has at least one beam-limiting aperture apparatus that provides an aperture through which the beam must pass to reach the sample. The aperture apparatus is adjustable to vary at least one of the cross section and the position of the aperture by movement of a single movable component of the aperture apparatus in one direction. The movable component may be an aperture medium that is substantially opaque to the radiation beam and within which a plurality of holes are located. Movement of the aperture medium relative to the radiation beam changes which one of a plurality of different holes is located in the beam path. The different holes may be at different positions relative to the beam and may have different sizes or shapes.

In one embodiment of the invention, the aperture apparatus comprises a disk that can be rotated about an axis. The disk uses a material that is not transparent to the beam radiation and that has a plurality of holes that are positioned within a radial range from $r_{min}$ to $r_{max}$ relative to a center of the disk. The disk may be positioned with a primary surface perpendicular to the beam, and the holes are arranged such that rotation of the disk by a predetermined angular increment changes the hole that is in the path of the beam. The disk may also be arranged such that, in each rotational position, taking into account the maximum beam cross-section at that position, radiation passes through only one of said holes. Some of the holes may have an identical cross-section, but different radial positions within the range $r_{min}$ to $r_{max}$, such that the transition from one hole to another one results in a radial shift of the effective aperture. As each of the holes passes through the range of the beam, rotation of the disk also results in a change in the angular position of that hole. Thus, the apparatus allows a shift of the aperture in two dimensions by only one movement, namely, the rotation of the disk.

In another embodiment of the invention, the aperture apparatus comprises a tape of width $b_s$ that resides in a plane that intersects the beam direction, and that can be shifted across the beam path in a first direction. As with the disk, the tape is made from material that is not transparent to the beam radiation, and the tape has a plurality of holes located at different positions along a second direction perpendicular to the first direction. Holes at different positions along this second direction, or width, of the tape therefore intersect the beam in different regions of the beam cross section. These positions may span a given range, such as between $b_{min}$ and $b_{max}$, and holes at each of these positions produce an output beam at a different positional shift along the second direction. Thus, by moving the tape along the first direction by a given increment, holes at different positions along the second direction may be positioned to intersect the beam, and to thereby produce an output beam with a different positional shift. As with the disk embodiment, the holes in the tape may be arranged relative to one another, taking into account the maximum beam cross-section at the tape position, so that radiation passes through only one of the holes at a time in a direction that can reach a sample being analyzed. The holes may have an identical cross-section but different width positions between $b_{min}$ and $b_{max}$, such that, as mentioned above, the transition from one hole to the next can be used to effect a positional shift in the effective aperture in the second direction. While the beam is illuminating a given hole, a slight shift of the tape in the first direction results in the output from a hole in the path of the beam to be shifted in the first direction, thereby allowing a positional shift of the effective aperture in the first direction. Thus, shifting of the aperture in two dimensions may be accomplished by changing only one parameter, namely, the movement of the tape in the first direction.

In the tape embodiment, the tape may be controlled by winding two opposite ends of the tape on take-up reels positioned to opposite sides of the beam. The tape is held under tension between the reels, and its position may be shifted by rotating one of the reels, for example, by using a motor attached by a shaft to the reel. The plane of the tape which intersects the beam path, may be kept in a desired orientation relative to the beam by using guides through which the tape must pass and which keep the relevant portion of the tape at the desired orientation. The guides might also include a guide that has a closed loop shape in a plane perpendicular to the beam such that the beam passes through the closed loop of the guide. In such a case, the guide may also serve as a maximum aperture for the beam while a hole that is within the cross section of the beam is located within the closed loop shape of the guide.

The tape may also be mounted in a cassette, similar to an audio or video cassette, which may be exchangeable in the analysis apparatus. The cassette housing is configured such that it does not interfere with the beam, which passes through it to encounter the tape. For example, the cassette itself may have apertures that align with the relevant portion of the tape along the path of the beam. The use of a cassette allows for a simple exchange of different tapes having different hole configurations. In one variation of this embodiment, the tape itself is configured as a closed loop that may be repeated drawn through the path of the beam in the same direction. This allows different positions on the tape to be repeatedly accessed while moving the tape loop in only one direction. The loop may also be in the shape of a Möbius band, such that, after one revolution, upper and lower parts of the tape are reversed, providing twice as many (symmetric) positions of the holes.

It may be desirable to have a total number of holes in the disk or the tape be greater than 12, or even greater than 36. When using the disk, the number of holes may be limited by the surface area of the disk and the radial positioning of the holes. When using a tape, there is no such limitation on the number of holes, which may number much higher, e.g., in the hundreds. The larger the number of holes, the more precisely the beam can be shifted in the second dimension and/or the number of different hole cross-sections can be increased.

In one example, the holes may be aligned in rows, each with a particular number of holes. For example, there may be j rows, each with i holes. Each of the rows may have holes that all have an identical cross-section, but that are all positioned slightly differently. Thus, a desired cross section may be shifted in two directions by changing the position of the disk or tape along the range of a given row.

It may be desirable to locate the holes of a row, in a dimension perpendicular to the movement of the medium, so that the hole position from one hole to the next changes incrementally in a constant direction. On a disk, this would be effected by locating each hole in a row slightly further from the center of the disk than an adjacent hole. On a tape, each hole of a given row could be offset incrementally further along the second direction than a previous hole. This arrangement would allow the position of a beam to be shifted incrementally in a quasi-continuous manner by shifting from one hole to the next of a given row. Such shifts of the beam position may be particularly useful for illuminating or obscuring different parts of focusing optics, which may influence the magnification ratio of the optics.

It may also be desirable to arrange the holes such that the number of holes on the disk or tape is maximized with the constraint that, in each position of the disk or tape, the beam does not pass through two neighboring holes simultaneously. Similarly, the holes may be configured such that a given hole can be moved within the beam width, perhaps across the entire beam cross-section, without radiation passing through a neighboring hole simultaneously. This "closest packing" of the holes allows the most compact arrangement of holes for a given amount of hole sizes and/or positions.

In the analysis system, it may be desirable to provide at least one fixed aperture in the beam path, in particular directly before and/or behind the disk or tape. The cross-section of this aperture may be matched to the largest available beam cross-section and/or to the cross-section of the largest hole. The fixed aperture may also be sized to match the extent of the range of the holes in the direction perpendicular to the movement direction of the aperture medium, such as the range $r_{max}-r_{min}$ for the disk, or $b_{max}-b_{min}$ for the tape. Altogether an aperture in the form of a broad gap is preferred. This fixed aperture can also be exchangeable.

In one implementation of the invention, the variable aperture is positioned in the analysis system in the beam path between source and focusing optics. In one variation, the variable aperture is positioned close to the focusing optics, and possibly directly before the focusing optics. With this arrangement the beam divergence can be adjusted optimally. The variable aperture may also be positioned in the beam path between the focusing optics and the sample, possibly close to the focusing optics, or even directly behind the focusing optics. The variable aperture may also be positioned in the beam path directly before the sample to enable an optimal illumination and/or masking.

The variable aperture apparatus may also be driven by a motor, and its movement may be controlled by a controller. The motor may be, for example, a stepper motor. This would allow a particularly precise adjustment of the desired positions. The positions may also be pre-set and/or stored for renewed alignment. To this end, the system may also include a sensor for determining the position of the variable aperture. An optical sensor in combination with an encoder may be attached to the variable aperture to detect the position of the aperture medium, or the sensor may detect position based on detection of the position of those holes that are not currently in the path of the beam. The aperture apparatus may also be configured to allow the easy exchange of aperture media.

BRIEF DESCRIPTION OF THE DRAWINGS

The above and further advantages of the invention may be better understood by referring to the following description in conjunction with the accompanying drawings in which:

FIG. 2b is a schematic, front view of a disk such as that used in the apparatus of FIG. 2a;

FIG. 3 is a schematic view of a variable aperture medium in the form of a tape;

DETAILED DESCRIPTION

Figure 1:
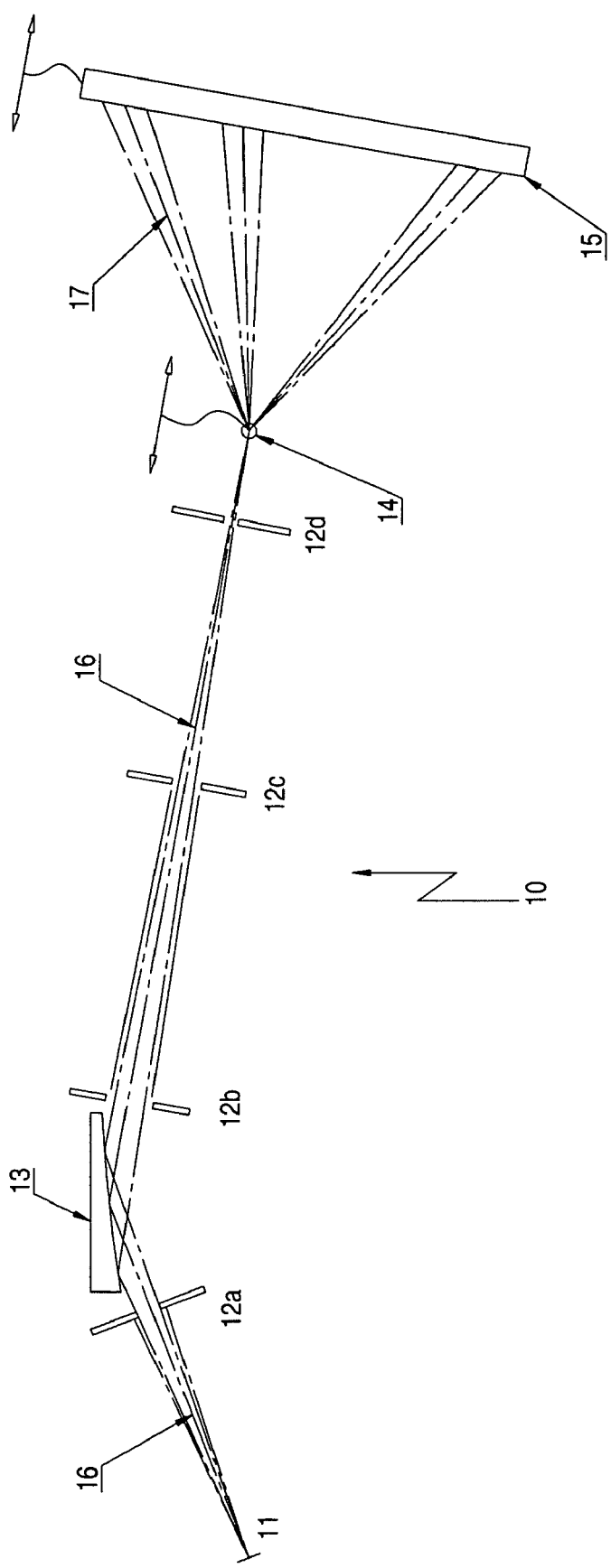
FIG. 1 is a schematic view of an X-ray beam analysis system that uses a variable aperture according to the invention.

Shown schematically in FIG. 1 is an analysis device 10 according to the invention which comprises a single crystal diffractometer. A sample 14, in particular a single crystal, is illuminated by an X-ray beam 16 via focusing X-ray optics 13 which, in this embodiment, may be an X-ray mirror and, more particularly, a multilayer mirror such as a Göbel mirror or a Montel mirror. The focus of the beam 16 may be chosen to be on the sample or, alternatively, on detector 15 located behind the sample 14. The optimal position of the beam focus depends on the required experimental conditions. X-rays 17 scattered by the sample 14 are detected by the detector 15, which may be an area detector. A diffraction pattern of the sample is formed on the detector surface, and is detected and resolved by the detector and evaluated in a subsequent processing step.

Positioned at several locations along the path of the X-ray beam 16 are apertures or masks 12a-12d through which the beam 16 must pass. A first aperture 12a is located immediately before the X-ray optics 13 along the beam path, a second aperture 12b is located after the X-ray optics 13 but in close proximity, a third aperture 12c is located further along the beam path toward the sample, and a fourth aperture 12d is located even further along the path, in close proximity to the sample 14. In this embodiment, apertures 12b and 12c are attached to each other and combine to form an expanding conical pipe, although this configuration is not necessary to the invention. Each of the apertures 12a-12d is either fixed or exchangeable, and at least one of the apertures is a variable aperture.

Figure 2A:
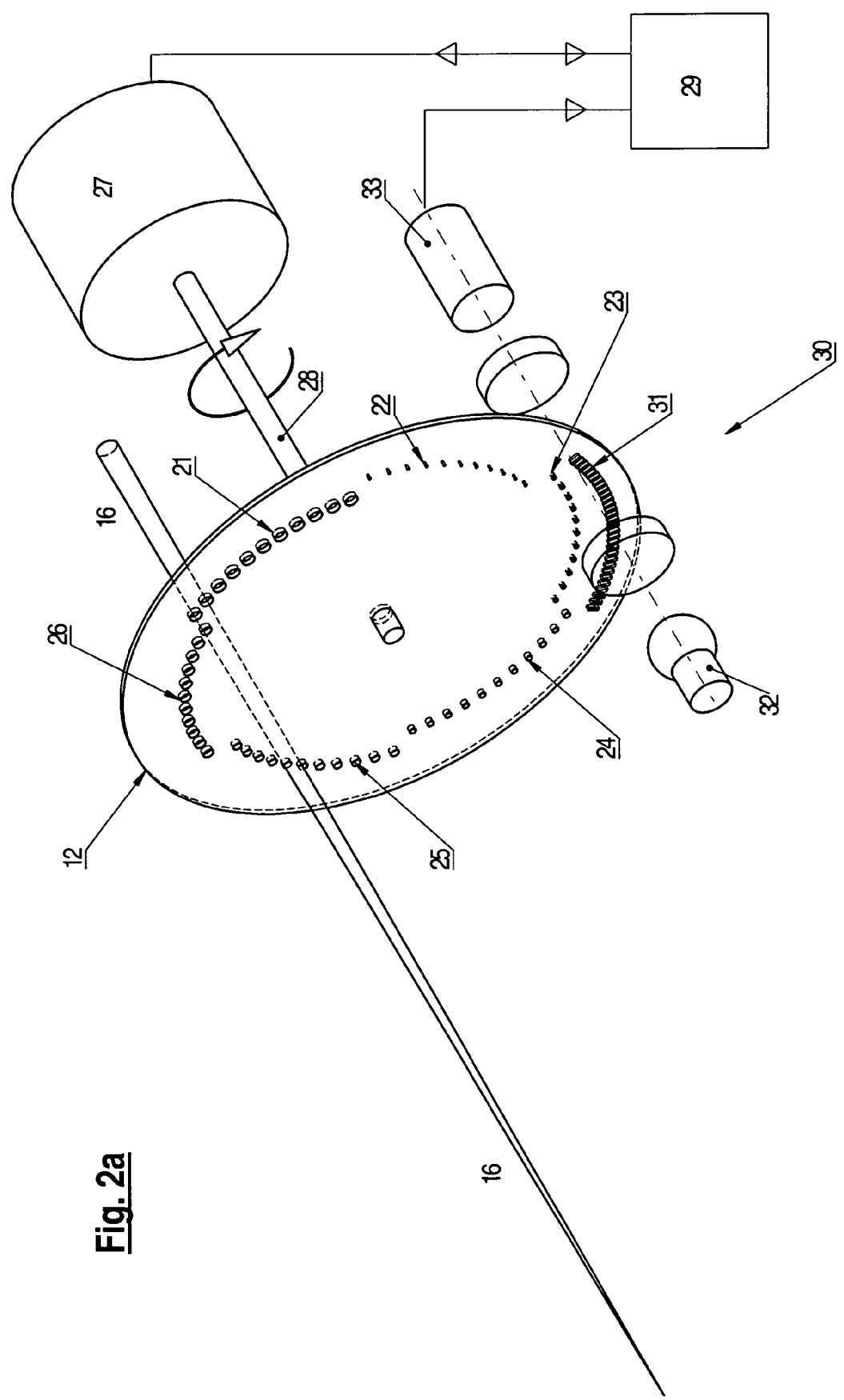
FIG. 2a is a schematic, perspective view of a variable aperture apparatus having a disk-shaped aperture medium.
Figure 2B:
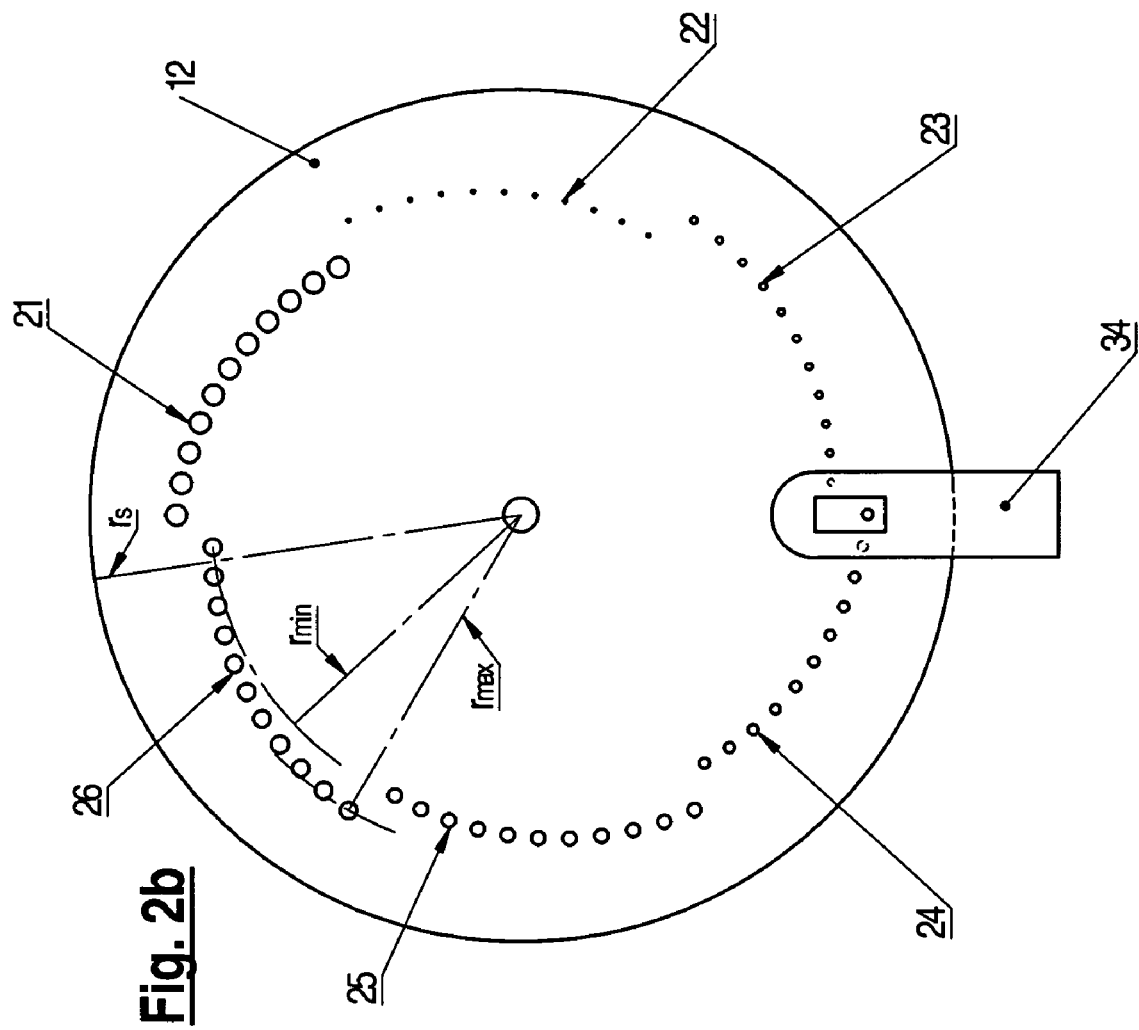

FIGS. 2A and 2B show components of a first embodiment of a variable aperture according to the invention that may be used in a system like that of FIG. 1. In this embodiment, the aperture is a perforated disk 12 with radius $r_s$. The disk 12 comprises a material that is not transparent for the X-ray wavelengths used, typically some type of metal. The particular material, and its thickness, may be selected based on known data for common materials for the particular X-ray radiation used, which may be, for instance, Cu-$K_{alpha}$ radiation. Along the face of the disk are a plurality of rows 21, 22, 23, 24, 25, 26 of holes, each of which is arranged so that it follows a path of changing radius relative to the center of the disk. In the example shown in FIGS. 2A and 2B, the total number "j" of rows is equal to 6, and each row is at a radius $r_{min}$ at one end of the row, and at a radius $r_{max}$ at the other end of the row. In the example shown, the total number of holes "i" for each row is equal to eleven, and each row has the same average radial distance to the center of the disk. In addition, the rows have an equal relative angular spacing about the disk. However, those skilled in the art will recognize that the specific configuration of holes on the disk may be varied as appropriate for a particular application.

As shown in FIG. 2A, the surface of disk 12 is oriented roughly perpendicularly to the beam 16, and the positions and distances between the holes are such that, when the angular position of a hole is aligned with the angular position of the beam only one hole is illuminated. Alternatively, the distances between the holes are slightly larger, such that each hole can be somewhat moved perpendicular to the beam without illuminating a neighboring hole. The disk 12 may be rotated using a motor 27, which is controlled by controller 29 of the analysis device 10. The motor 27 drives a disk shaft 28, which brings the holes into the path of the beam. Each hole can be aligned around the beam center in the angular direction, and the angular position of the transmitted beam can be varied in the range of the beam cross-section by slightly varying the angular position of the hole.

While holes of the same row are being sequentially exposed to the beam, rotation of the disk causes a shift in radial position of the transmitted beam due to the transition between neighboring holes. Each of the holes of a given row has a slightly different radial position so, with each hole, a different portion of the beam is transmitted through the disk, and each of these beam portions is also at a different radial position. The effective result is, therefore, that changing from one hole to the next changes the radial position of the beam exiting the aperture. In the example shown, there are six rows of holes, each row having holes with a cross-section that differs from the holes of the other rows. Within a given row, the holes all have the same cross section, but differ from one another by their radial position. These characteristics, of course, are specific to this example, and those skilled in the art will understand that the arrangement and cross section of the holes may take on any of a number of different configurations. Similarly, although the cross-sectional shape of the holes in the disk 12 is circular, the holes may just as well be square or elliptical, as may be desired. Moreover, the disk may be tilted relative to a plane perpendicular to the beam direction, thereby changing the effective cross-sectional shape of the holes (e.g., circular holes would effectively become elliptical holes). A variation such as this may also be applied, if desired.

A positional marking may also be delineated on the disk, and used for monitoring the disk position. In the example shown in FIGS. 2A and 2B, the marking 31 consists of a series of perforations in the disk at a radial distance further from the center of the disk than the rows of holes. This marking may be read by a device such as an optical scanner, represented in the figure by light source 32 and detector 33. The detection of the code with the optical scanner may be used to identify the angular position of the disk 12 and to generate a signal to the controller 29 indicative thereof. The controller may thereby use that information to control the angular position of the disk. As an example, a disk position read from the code may be used to establish a zero-position for the stepper motor 27.

Depending on the desired beam profiles and beam positions, different disks 12 may be attached to the shaft 28, the different disks having different arrangements of holes. If desired, different constraints may be maintained from one disk to the next, such as requiring that, during measurement, only one hole is illuminated by beam 16 at a given time. The various configurations, however, may be within the control of a system user.

As shown in FIG. 2B, there may also be a limiting aperture 34 directly in front of or behind the disk 12 that limits the cross section of the beam that is actually encountered by the disk. In the example shown in the figure, the limiting aperture 34 is sized to cover only the range of $r_{max}$-$r_{min}$, which is the range over which the radial position of the holes on the disk varies. This limiting aperture 34 remains stationary as the disk rotates and, optionally, may be exchangeable with other apertures. In this example, the limiting aperture 34 has a width that corresponds to, or is slightly larger than, the maximum width of a hole adjacent to it. Different limiting apertures may also be used as may be appropriate with a particular embodiment.

The disk-shaped aperture medium of FIGS. 2A and 2B provides a basis for variable apertures that may be used in the example of FIG. 1 as one or more of the apertures 12a-12d. Another type of variable aperture according to the present invention uses an aperture medium that may be moved linearly, rather than rotationally. FIG. 3 is a schematic depiction showing a perforated tape 36 that is a part of a second embodiment of the present invention. The tape 36 has rows of holes along its length, and it may be shifted in the x-direction indicated in the figure. The rows 38, 40, 42, 44 and 46 of holes vary in position along the y-direction, which is perpendicular to the x-direction. In this example, each row has holes that are of a constant cross section, and that vary in position incrementally relative to the y-direction. As the tape is moved in the x-direction, the y-direction may be viewed as being along the width of the tape. If the tape is illuminated with an X-ray beam, and only one of the holes is in the path of the beam at a given time, the beam exiting the other side of the tape will have a position along the y-direction that depends on which hole is in the path of the beam. Shifting the tape to move one hole of a row out of the beam path, and to move another hole of that row into the beam path, has the effect of shifting the position of the output X-ray beam in the y-direction. Shifting a different row into the path of the beam has the effect of changing the cross-sectional size of the output beam. In the example of FIG. 3, each of the rows has j=10 holes in different positions along that width from a lower limit $b_{min}$ to an upper limit $b_{max}$.

For the tape embodiment, the number of rows can be significantly larger than the number of rows used for the disk embodiment of FIGS. 2A and 2B. Otherwise, the tape embodiment of FIG. 3 operates in a manner analogous to the embodiment of FIGS. 2A and 2B, where the shift of the FIG. 3 tape in the x-direction corresponds to a rotation of the FIGS. 2A and 2B disk. Similarly, the distance in the y-direction spanned by the holes in the tape 36 corresponds to the distance spanned by the holes along a radial dimension of the disk of FIGS. 2A and 2B. The FIG. 3 embodiment may also use at least one limiting aperture 48 that is similar to the aperture 34 shown in FIG. 2B. Like the disks, tapes can also be exchanged if necessary and can be mounted at any of the aperture positions 12a-12d shown in FIG. 1. Depending on the manner of tape transport, the flexibility of the material and thickness of the tape may vary. In general, the desired tape thickness depends on the type of radiation used and by the tape material itself.

Figure 4:
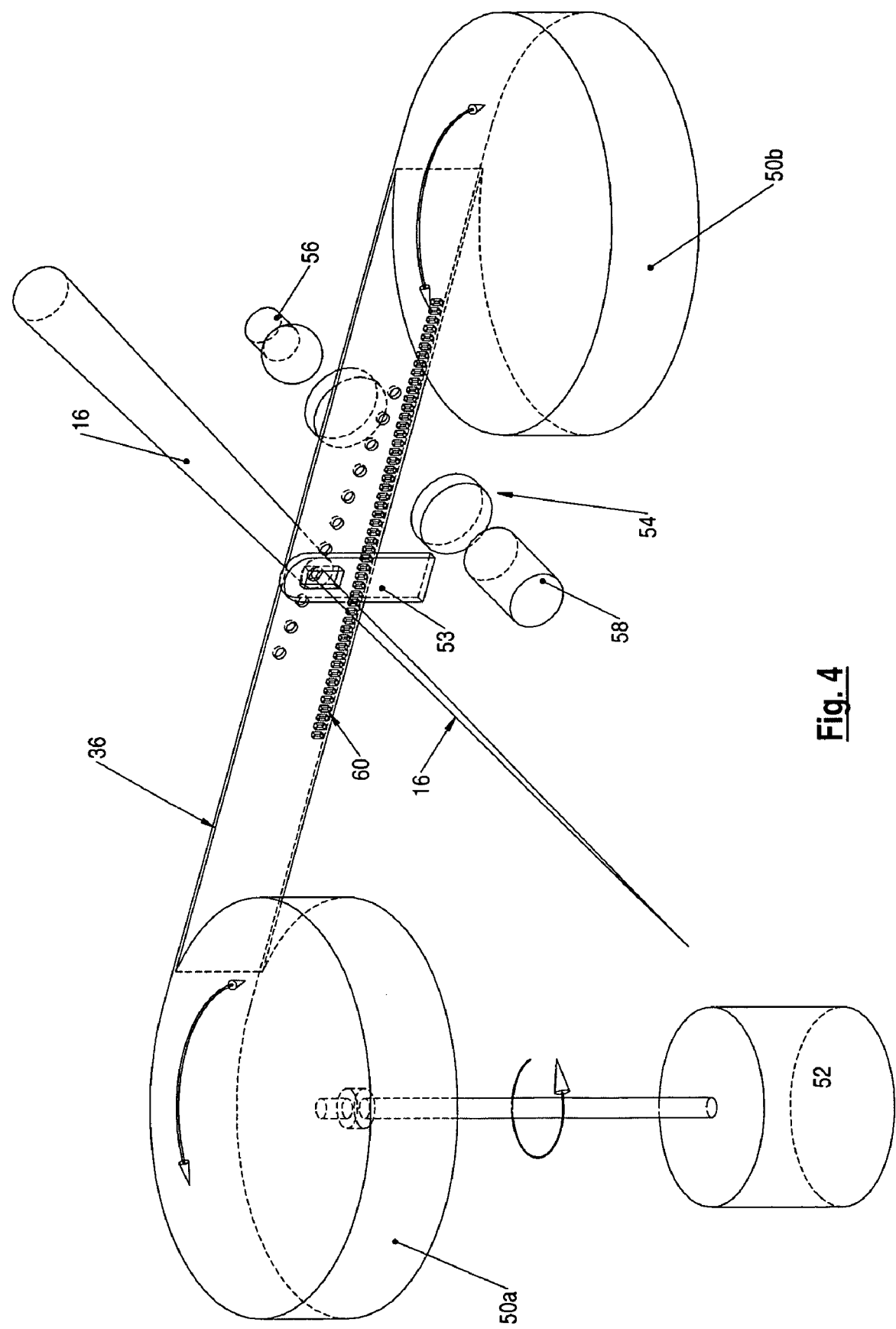
FIG. 4 is a schematic, perspective view of a variable aperture apparatus that may use the tape shown in FIG. 3.

FIG. 4 shows an embodiment of a tape transport system for use with an aperture tape like that of FIG. 3. In this embodiment, the tape 36 is wound under tension about two axes, in this example, making use of take-up reels 50a and 50b. The rotation of the take-up reels may be driven by a motor 52 that may be connected to one of the reels via a drive shaft. The two take-up reels 50a, 50b, together with fixed aperture guide 53, keep the tensioned tape straight and perpendicular to the beam 16 in the area where the beam 16 encounters the tape. The beam passes through limiting aperture 48, as discussed above. A tape position sensor 54 may make use of a light source such as LED 56 and a detector 58. By illumination of a set of markings 60, which may comprise a line of holes in the tape 36, and detection of the light passing through the holes, the tape position may be monitored and used by a controller to control the motor 52.

Figure 5:
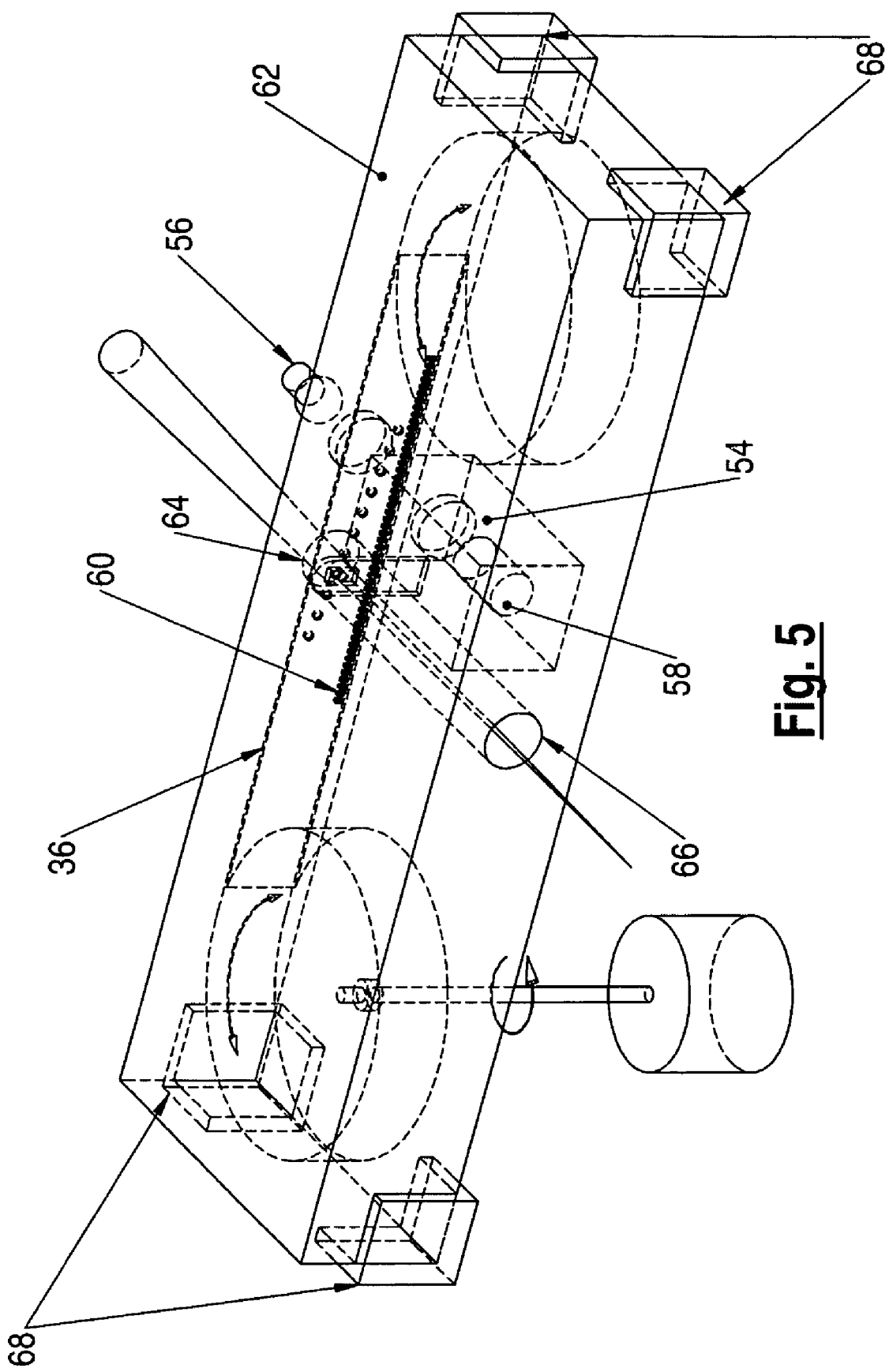
FIG. 5 is a schematic, perspective view of a cassette mechanism that may be used with the variable aperture apparatus of FIG. 4.

FIG. 5 shows the tape system of FIG. 4 mounted in a cassette 62 that houses the system components. The tape 36 may be wound back and forth between the take-up reels, which are mounted inside the cassette. In this example, the cassette 62 also houses the detector 58 used by the tape position sensor, although those skilled in the art will understand that the detector may also be mounted outside of the cassette, for example, in an adjacent analysis device. The cassette housing itself contains two separate apertures 64, 66, which allow the beam to pass into the cassette to where it encounters the tape 36, and then out the other side. Mounting brackets 68 may be used to accurately position the cassette in the system.

Figure 6:
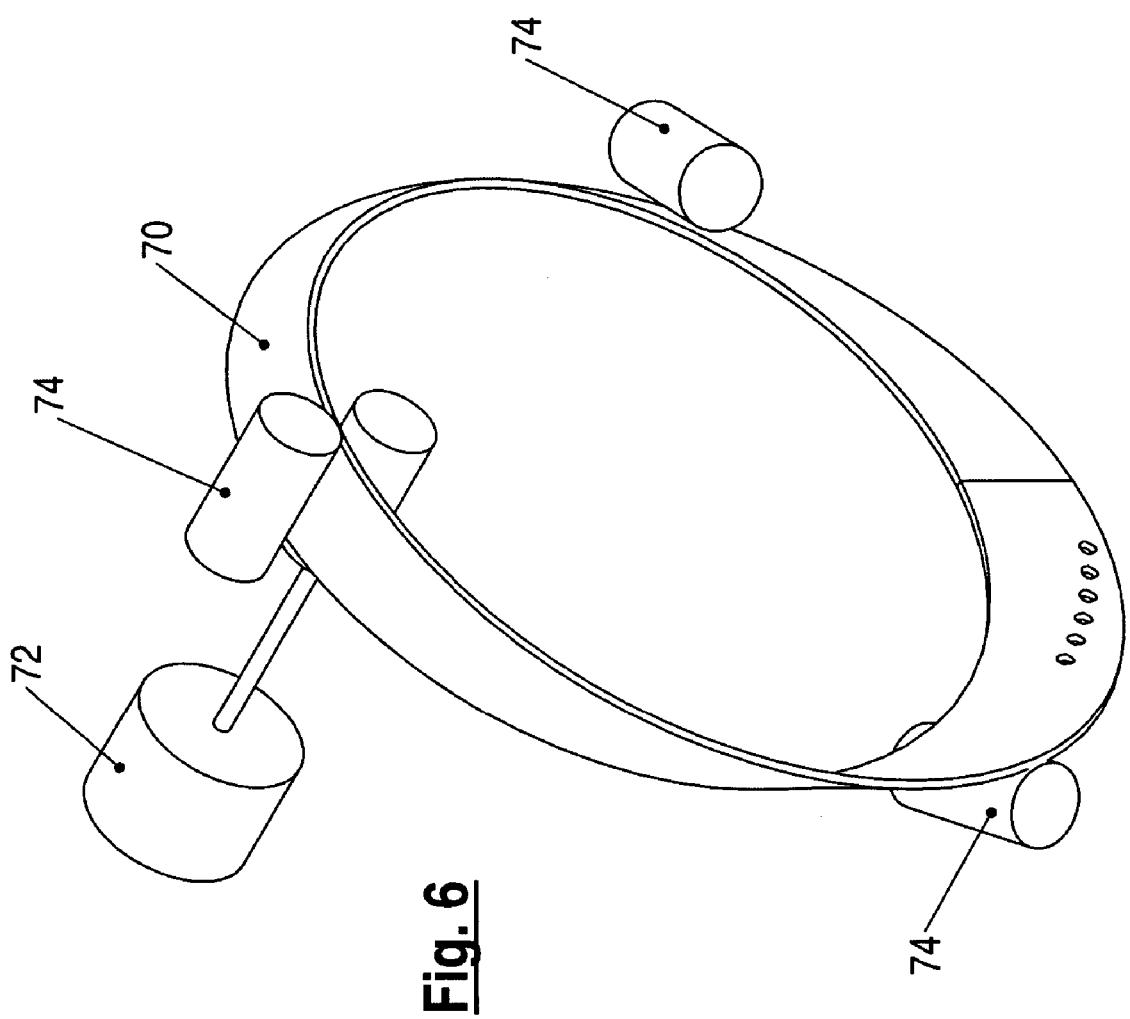
FIG. 6 is a schematic, perspective view of a variable aperture medium in the form of a tape shaped like a Möbius band.

A variation of the reel-to-reel tape embodiment of FIGS. 4 and 5 is shown FIG. 6. In this embodiment, a tape 70, rather than being linear and rolled onto take-up reels, may be implemented as a closed loop. In this example, the movement of the tape may be driven by a motor 72 and guided by several drums 74. In the area where the beam meets the tape, the tape will be flat and perpendicular to the beam. However, in this example, the tape is in the shape of a Möbius band. Thus, after one revolution the positions of the front and back side of the tape, and the upper and lower edge of the tape, are exchanged. Thus, if the holes in the tape are biased to one side along the width of the tape, one revolution of the tape reverses those positions along the tape width. This effectively doubles the number of positions for holes along the tape width, and provides the system with greater versatility for a given length of tape. Those skilled in the art will recognize that the other characteristics discussed for the previous examples apply in a corresponding way to this embodiment of a variable aperture.

While the invention has been shown and described with reference to the embodiments thereof, those skilled in the art will recognize that various changes in form and detail may be made herein without departing from the spirit and scope of the invention as defined by the appended claims.

What is claimed is:

1. An X-ray diffraction apparatus comprising:
   an X-ray generator for generating an X-ray beam that propagates in a beam direction to illuminate a sample in order to make an X-ray diffraction measurement;
   a movable component having a plurality of apertures with identical sizes and shapes, but located at different positions along a first direction perpedicular to the beam direction, the component being positioned between the generator and the sample so that the X-ray beam illuminates the sample through a single first aperture; and
   a mechanism for moving the component in a second direction different from the first direction to cause the X-ray beam to illuminate the sample through another single aperture with a position that is shifted in the first and second directions from the position of the first aperture.

2. An apparatus according to claim 1 wherein the movable component comprises an aperture medium that is substantially opaque to the X-ray beam and within which a plurality of holes are located.

3. An apparatus according to claim 2 wherein the aperture medium comprises a disk that is moved rotationally.

4. An apparatus according to claim 3 wherein rotation of the disk by a predetermined angular distance moves a first one of the holes out of alignment with the beam and a second one of the holes into alignment with the X-ray beam.

5. An apparatus according to claim 4 wherein the second hole has a different radial position than the first hole relative to an axis about which the disk is rotated.

6. An apparatus according to claim 5 wherein at least some of the holes in the disk are aligned in a row that, from one end of the row to an opposite end, is characterized by the incremental increase in radial position of the holes in the row relative to an axis about which the disk is rotated.

7. An apparatus according to claim 6 wherein all of the holes of the row have the same cross-sectional size and shape.

8. An apparatus according to claim 6 wherein the row is a first row and wherein the holes of the disk are organized into a plurality of rows located in different radial segments around the disk.

9. An apparatus according to claim 8 wherein the holes of a given row all have the same cross-sectional size as each other, and a cross-sectional size different from that of the holes in the other rows.

10. An apparatus according to claim 4 wherein the disk rotation is driven by a motor.

11. An apparatus according to claim 10 further comprising a position sensor that detects indicia of the disk to determine the rotational position of the disk.

12. An apparatus according to claim 11 wherein the indicia comprise the holes of the disk.

13. An apparatus according to claim 11 further comprising a controller that controls the position of the disk so as to align a chosen one of the holes with the beam.

14. An apparatus according to claim 2 wherein the aperture medium comprises a tape that is moved in a linear direction in the vicinity of the beam.

15. An apparatus according to claim 14 wherein movement of the tape by a predetermined distance moves a first one of the holes out of alignment with the beam and a second one of the holes into alignment with the beam.

16. An apparatus according to claim 15 wherein the second hole has a different lateral position than the first hole relative to a direction perpendicular to the direction along which the tape is moved in the vicinity of the beam.

17. An apparatus according to claim 16 wherein at least some of the holes in the tape are aligned in a row that, from one end of the row to an opposite end, is characterized by the incremental increase in lateral position of the holes in the row relative to a direction perpendicular to the direction along which the tape is moved in the vicinity of the X-ray beam.

18. An apparatus according to claim 17 wherein all of the holes of the row have the same cross-sectional size and shape.

19. An apparatus according to claim 17 wherein the row is a first row and wherein the holes of the tape are organized into a plurality of rows located in different linear segments along the length of the tape.

20. An apparatus according to claim 19 wherein the holes of a given row all have the same cross-sectional size as each other, and a cross-sectional size different from that of the holes in the other rows.

21. An apparatus according to claim 15 wherein the tape movement is driven by a motor.

22. An apparatus according to claim 15 wherein the tape is wound onto take-up reels that are rotated to move the holes on the tape relative to the X-ray beam.

23. An apparatus according to claim 22 further comprising a position sensor that detects indicia of the tape to determine the position of the tape relative to the X-ray beam.

24. An apparatus according to claim 23 wherein the indicia comprise the holes of the tape.

25. An apparatus according to claim 23 further comprising a motor that drives one of the take-up reels and a controller that controls the motor to position the tape so as to align a chosen one of the holes with the X-ray beam.

26. An apparatus according to claim 22 further comprising a cassette within which the tape and take-up reels are housed, the cassette having apertures that allow the X-ray beam to enter a first side of the cassette, encounter the tape, and exit a second side of the cassette.

27. An apparatus according to claim 15 wherein the tape forms a closed loop.

28. An apparatus according to claim 27 wherein the tape forms a Möbius loop.

29. An apparatus according to claim 2 wherein the aperture medium has a minimum of thirty-six holes.

30. An apparatus according to claim 1 further comprising at least one fixed aperture positioned between the generator and the sample along with the movable component.

31. A method for operating an X-ray diffraction apparatus, the method comprising:
   generating an X-ray beam that propagates in a beam direction to illuminate a sample in order to make an X-ray diffraction measurement;
   positioning a movable component between the generator and the sample, the movable component having a plurality of apertures with identical sizes and shapes, but located at different positions along a first direction perpendicular to the beam direction, so that the X-ray beam illuminates the sample through a single first aperture; and
   moving the component in a second direction different from the first direction to cause the X-ray beam to illuminate the sample through another single aperture with a position that is shifted in the first and second directions from the position of the first aperture.

* * * * *